US010639479B2

(12) United States Patent
Dinsmoor et al.

(10) Patent No.: US 10,639,479 B2
(45) Date of Patent: May 5, 2020

(54) STIMULATION VECTOR SELECTION USING PULSE WIDTH DATA

(71) Applicant: Medtronic, Inc., Minneapolis, MN (US)

(72) Inventors: David A. Dinsmoor, North Oaks, MN (US); Xin Su, Plymouth, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 145 days.

(21) Appl. No.: 15/804,719

(22) Filed: Nov. 6, 2017

(65) Prior Publication Data

US 2018/0133484 A1    May 17, 2018

Related U.S. Application Data

(66) Substitute for application No. 62/420,910, filed on Nov. 11, 2016.

(51) Int. Cl.
*A61N 1/36* (2006.01)
*A61N 1/37* (2006.01)
*A61N 1/372* (2006.01)

(52) U.S. Cl.
CPC ..... *A61N 1/36175* (2013.01); *A61N 1/36007* (2013.01); *A61N 1/36062* (2017.08);
(Continued)

(58) Field of Classification Search
CPC ...... A61N 1/368; A61N 1/3684; A61N 1/371; A61N 1/3712
See application file for complete search history.

(56) References Cited

U.S. PATENT DOCUMENTS

2012/0197338 A1   8/2012  Su et al.
2012/0277621 A1*  11/2012  Gerber ................. A61B 5/0031
                                                        600/554
(Continued)

OTHER PUBLICATIONS

Brink, et al., "A Chronic, Conscious Large Animal Platform to Quantify Therapeutic Effects of Sacral Neuromodulation on Bladder Function," J Urol. Jul. 2015;194(1)pp. :252-258. doi: 10.1016/j.juro.2015.01.109. Epub Feb. 2015.
(Continued)

*Primary Examiner* — Michael J D Abreu
(74) *Attorney, Agent, or Firm* — Patterson Thuente Pedersen, P.A.

(57) ABSTRACT

A method of programming an implantable medical device (IMD) configured to provide electrical stimulation via a plurality of stimulation vectors during delivery of the electrical stimulation of a plurality of pulse widths to a neural target. The method may comprise comparing strength-duration curve data for the plurality of stimulation vectors to one another, the strength-duration curve data representing, for respective pulse widths and stimulation vectors, a corresponding stimulation strength that evokes a physiological response associated with the neural target. The method may comprise selecting at least one stimulation vector of the plurality of stimulation vectors based on the comparison of the strength-duration curve data for the plurality of stimulation vectors. The method may comprise programming, in response to the selection, the IMD to deliver the electrical stimulation to the neural target via the selected at least one stimulation vector.

11 Claims, 8 Drawing Sheets

(52) U.S. Cl.
CPC ..... *A61N 1/36071* (2013.01); *A61N 1/36125* (2013.01); *A61N 1/36171* (2013.01); *A61N 1/3708* (2013.01); *A61N 1/37247* (2013.01)

(56) References Cited

U.S. PATENT DOCUMENTS

| | | |
|---|---|---|
| 2013/0289659 A1 | 10/2013 | Nelson et al. |
| 2015/0335893 A1 | 11/2015 | Parker |
| 2016/0082265 A1 | 3/2016 | Moffitt et al. |
| 2016/0121123 A1 | 5/2016 | Jiang et al. |

OTHER PUBLICATIONS

Cohen, et al., "Predictors of success for first stage neuromodulation: motor versus sensory response," J Urol. 2006 Jun. 2006;175(6): pp. 2178-2180; discussion 2180-1.

Dudding et al., "Predictive factors for successful sacral nerve stimulation in the treatment of faecal incontinence: a 10-year cohort analysis" Colorectal Dis. Mar. 2008;10(3):249-56. Epub Jul. 26, 2007.

Everaert et al., "Patient satisfaction and complications following sacral nerve stimulation for urinary retention, urge incontinence and perineal pain: a multicenter evaluation" Int Urogynecol J Pelvic Floor Dysfunct. 2000;11(4): pp. 231-236; discussion 236.

Evers et al., "Effects of stimulation frequency and intensity in sacral neuromodulation on anorectal inputs to the somatosensory cortex in an experimental model," Br J Surg. Sep. 2014;101(10):pp. 1317-1328. doi: 10.1002/bjs.9587. Epub Jul. 28, 2014.

Govaert et al., "Can sensory and/or motor reactions during percutaneous nerve evaluation predict outcome of sacral nerve modulation?," Dis Colon Rectum. Aug. 2009;52(8): pp. 1423-1426. doi: 10.1007/DCR.0b013e3181a91241.

Grill Jr. et al. "Stimulus waveforms for selective neural stimulation," IEEE Engineering in Medicine and Biology Magazine. Jul./Aug. 1995, vol. 14, Issue: 4, pp. 375-385, DOI: 10.1109/51.395310.

Grill Jr. et al., "The effect of stimulus pulse duration on selectivity of neural stimulation," IEEE Trans Biomed Eng. Feb. 1996;43(2): pp. 161-166.

Hamdy et al., "Laterality effects of human pudendal nerve stimulation on corticoanal pathways: evidence for functional asymmetry," Gut. Jul. 1999;45(1):pp. 58-63.

Lee J, Osann K, Noblett K. "Comparison of motor and sensory response of InterStim® for overactive bladder syndrome," Female Pelvic Med Reconstr Surg. Nov.-Dec. 2013;19(6):pp. 317-321. doi: 10.1097/ SPV.0b013e3182a2954e.

McLennan, "The role of electrodiagnostic techniques in the reprogramming of patients with a delayed suboptimal response to sacral nerve stimulation," Int Urogynecol J Pelvic Floor Dysfunct. Jun. 2003;14(2):pp. 98-103. Epub Mar. 12, 2003.Nowak and Bullier, 1998.

Nowak et al., "Axons, but not cell bodies, are activated by electrical stimulation in cortical gray matter., I. Evidence from selective inactivation of cell bodies and axon initial segments." Exp Brain Res. Feb. 1998;118(4): pp. 489-500.

Ranck, Jr. "Which elements are excited in electrical stimulation of mammalian central nervous system: a review," Brain Res 98: May 1975, pp. 417-440.

Peters, et al., "Effect of Sacral Neuromodulation Rate on Overactive Bladder Symptoms: A Randomized Crossover Feasibility Study," LUTS: Lower Urinary Tract Symptoms May 2013; 5:pp. 129-133.

Schmidt, M.D., "Clinical Value of Neurostimulation: A Urlogic Viewpoint," Female Urology, Chapter 58, Second Edition, Jan. 1996; pp. 643-655.

Snellings et al. "Effects of stimulation site and stimulation parameters on bladder inhibition by electrical nerve stimulation," BJU Int Aug. 2012; 110: pp. 136-143.

Stern et al., "Chronaxie Measurements in Patterned Neuronal Cultures from Rat Hippocampus," PLoS One. Jul. 17, 2015;10(7):e0132577. doi: 10.1371/journal.pone.0132577. eCollection 2015.

Su, et al., "Neuromodulation in a rat model of bladder micturition reflex," Am J Physiol Renal Physiol Nov. 2, 2011; 302: F477-F486.

Su MD, et al. "Optimization of Neuromodulation for Bladder Control in a Rat Cystitis Model," Neuromodulation. Jan. 2016;19(1): pp. 101-107. doi: 10.1111/ner.12360. Epub Oct. 30, 2015.

Szlavik et al., "The effect of stimulus current pulse width on nerve fiber size recruitment patterns," Med Eng Phys. Jul.-Sep. 1999;21(6-7):pp. 507-515.

Weil et al., "Novel test lead designs for sacral nerve stimulation: improved passive fixation in an animal model," J Urol. Aug. 2000;164(2): pp. 551-555.

Zbar, "Sacral neuromodulation and peripheral nerve stimulation in patients with anal incontinence: an overview of techniques, complications and troubleshooting," Gastroenterology Report, Apr. 2014, 9 pages.

Zhang, et al., "Neural pathways involved in sacral neuromodulation of reflex bladder activity in cats," Am J Physiol Renal Physiol Jan. 2013; 304:F710-717.

Schmidt, MD., "Advances in Genitourinary Neurostimulation," vol. 18, No. 6, 1986, pp. 1041-1044.

Schmidt, et al., "Micturition and the Male Genitourinary Response to Sacral Root Stimulation," Jul. 27, 1977; pp. 21-25.

Schmidt, MD, "Neural Prostheses and Bladder Control," Engineering in Medicine and Biology Magazine, Jun. 1983, pp. 31-36.

Schmidt, et al., "Applications of Neurostimulation in Urology," Neurourology and Urodynamics; 7:585-592, May 1988.

Schmidt, et al., "Neurostimulation and Neuromodulation: A Guide to Selecting the Right Urologic Patient," Eur Urol 1998 pp. 23-26.

Schmidt, et al., "Sacral Root Stimulation in Controlled Micturition," vol. 17, No. 2, September pp. 1979, 5 pages.

Schmidt, et al., "Urinary Bladder and Sphinctep Responses to Stimulation of Dorsal and Ventral Sacral Roots," vol. 16, No. 4, Jan. 1979, pp. 300-304.

Schmidt, et al., "Neuroprostheses in the Management of Incontinence in Myelomeningocele Patients," vol. 143, Apr. 1990, pp. 779-782.

Schmidt, et al., "Sacral Nerve Stimulation for Treatment of Refractory Urinary Urge Incontinence," vol. 162, Aug. 1999, pp. 352-357.

Schmidt, et al., "An Analysis of the Reflex Activity in the Cervical Sympathetic Trunk Induced by Myelinated Somatic Afferents," Pflugers Arch. 314; Sep. 8, 1969, pp. 175-198.

Tanagho, M.D., "Neural Stimulation for Bladder Control," Seminars in Neurology, vol. 8, No. 2, Summer 1988, pp. 170-173.

Tanagho, MD., "Electrical Stimulation," JAGS 38: pp. 352-355, Mar. 1990.

Tanagho, MD., "Bladder Pacemaker: Scientific Basis and Clinical Future," Urology, Dec. 1982, pp. 614-619.

Tanagho, et al., "Electrical Stimulation in the Clinical Management of the Neurogenic Bladder," The Journal of Urology, vol. 140, Dec. 1988, pp. 1331-1339.

Tanagho, et al., "Neural Stimulation for Control of Voiding Dysfunction: A Preliminary Report in 22 Patients with Serious Neuropathic Voiding Disorders," Urological Neurology and Urodynamics, vol. 142, Aug. 1989, pp. 340-345.

International Search Report and Written Opinion from International Application No. PCT/US2017/060529, dated Feb. 7, 2018, 14 pp.

\* cited by examiner

STIMULATION VECTOR SELECTION USING PULSE WIDTH DATA

This patent application claims the benefit of U.S. Provisional Patent Application No. 62/420,910, by Dinsmoor et al., entitled "STIMULATION VECTOR SELECTION BASED ON STRENGTH-DURATION CURVE DATA" and filed on Nov. 11, 2016, the entire content of which is incorporated herein by reference.

TECHNICAL FIELD

The disclosure relates to medical devices and, more particularly, to medical devices that may be configured to deliver electrical stimulation therapy.

BACKGROUND

Various pathological neuromuscular conditions, including some that are resistant to first-line forms of treatment such as pharmaceuticals or lifestyle modifications, may be successfully treated by implantable medical devices (e.g., neurostimulation devices) that apply electrical stimulation in part to motor or sensory neurons. Some illustrative areas for which neurostimulation devices may provide successful therapy are pain, urinary and fecal incontinence (e.g., an inability to control bladder and bowel function, respectively). Those problems affect people of all ages, genders, and races. Various muscles, nerves, organs, and conduits within the pelvic floor cooperate to collect, store and release bladder and bowel contents. A variety of disorders may compromise urinary tract and bowel performance, and contribute to incontinence. Many of the disorders may be associated with aging, injury, or illness.

Urinary incontinence, or degree of urgency associated with incontinence, may originate from disorders of portions of the peripheral or central nervous system which control the bladder micturition reflex. Nerve disorders may also lead to overactive bladder activities and/or may prevent proper triggering and operation of the bladder. Furthermore, urinary incontinence may also result from improper communication between the nervous system and the urethra.

Sacral neuromodulation (SNM) at the third sacral foramen (S3) is an FDA-approved therapy for urinary urge incontinence, urgency-frequency and fecal incontinence. The generally recommended pulse width value for SNM is 210 microseconds (μs).

SUMMARY

This disclosure describes devices, systems, and techniques for identifying stimulation vectors that are able to evoke therapeutic responses in sensory or motor neurons by neurostimulation with efficient pulse widths and/or enhanced therapeutic windows in terms of available amplitude range without inducing non-therapeutic side effects. Some examples may be directed to neurostimulation for managing incontinence (bladder incontinence and/or fecal incontinence) of a patient and/or other patient conditions. In some examples, processing circuitry of a medical device system is configured to acquire strength-duration curve data for each of a plurality of stimulation vectors, and select one or more of the stimulation vectors as preferred based on a comparison of vector-specific values for one or more metrics derived from the strength-duration curve data for the vectors.

Metrics derived from the strength-duration curve data for a stimulation vector may include area under the curve (AUC) (e.g., determined using an integral of the curve), slope (e.g., determined using a derivative of the curve at a particular point or as a slope relative to two points on the curve), or any other metric that characterizes the magnitude, curvature, and/or shape of the strength-duration curve. In general, stimulation vectors better targeted to the neuron target will be flatter, with lower amplitudes necessary for capture, including at shorter pulse-widths. Use of such a stimulation vector to deliver electrical stimulation therapy to a patient may facilitate efficacious stimulation with electrical pulses having more efficient, i.e., shorter, pulse widths and/or enhanced therapeutic windows.

For example, a medical device may be configured to deliver electrical stimulation therapy via a stimulation vector selected according to the techniques of this disclosure with pulse widths below the 210 μs pulse width generally used and recommended, such as in a range of 20 to 180 μs. Stimulation with pulse widths in or proximate to this range may evoke a similar therapeutic response as the conventionally used 210 μs, but using substantially less energy per pulse (e.g., approximately 20% to 90% less energy per pulse). Using the shorter pulse width may thereby substantially extend (e.g., approximately tripling) the life or the time between charges of a power source (e.g., a lithium ion battery) for an implanted medical device (e.g., an implanted neurostimulation device). Using the shorter pulse width may also increase the therapy window or operating range in terms of amplitude of neurostimulation that may be applied without evoking an undesirable or non-therapeutic response, such as stimulation of additional proximate tissues in a non-therapeutic manner (e.g., in an incontinence therapy application, evoking contraction of the semitendinosus muscle).

Various examples of the present disclosure relate to a method of programming an implantable medical device configured to provide electrical stimulation using a plurality of stimulation vectors addressable by the stimulator device during delivery of electrical stimulation of different pulse widths to a neural target. The method comprises comparing, by the medical device system, strength-duration curve data for the plurality of stimulation vectors, the strength-duration curve data representing, for respective pulse widths, a stimulation strength that evokes a physiological response associated with the neural target. At least one stimulation vector of the plurality of stimulation vectors is selected based on the comparison of the strength-duration curve data for the set of stimulation vectors. The stimulator device is programmed to deliver electrical stimulation to the neural target via the selected stimulation vector.

Certain examples are directed toward a medical device system that includes a stimulator device coupled to at least one multi-electrode lead and configured to address a plurality of stimulation vectors. Processing circuitry is configured to, for each stimulation vector of at least a subset of the plurality of stimulation vectors: determine, for each of a plurality of pulse width values, a respective threshold pulse amplitude value that evokes a physiological response indicative of target nerve modulation; generate, from the threshold pulse amplitude values, a strength-duration curve for the respective stimulation vector, determine a value for a metric from the strength-duration curve; compare the values of the metric for respective stimulation vector of the at least a subset; and select a stimulation vector from the plurality of stimulation vectors based on the comparison.

Various aspects of the present disclosure are directed towards a medical device or system that is used to create a strength-duration curve for each of the plurality of stimulation vectors. The strength-duration curve can be created by delivering, using the implantable stimulator device, electrical stimulation at different threshold pulse amplitudes, and by determining a threshold pulse amplitude value that evokes the physiological response for each one of a plurality of pulse width values. The medical device or system can then determine, for the strength-duration curves of the plurality of stimulation vectors, respective values for at least one metric, and then select at least one stimulation vector is based on a comparison between the values of the at least one metric.

Consistent with some examples, a method of programming a stimulator device of a medical device system comprises collecting, by the medical device system, strength-duration curve data for each stimulation vector of a plurality of stimulation vectors addressable by the stimulator device during delivery of electrical stimulation to a neural target via the stimulation vector, selecting at least one stimulation vector of the plurality of stimulation vectors based on a comparison of the strength-duration curve data for the set of stimulation vectors, and controlling the stimulator device to deliver electrical stimulation to the neural target via the selected stimulation vector.

In various examples, a method of operation of a stimulator device comprises delivering electrical stimulation to a neural target using a stimulation vector that is selected from a plurality of stimulation vectors addressable by the stimulator device based on a comparison of strength-duration curve data captured for each one of the plurality of stimulation vectors during delivery of stimulation to the neural target via the stimulation vector.

In some examples, a method comprises, for each stimulation vector of a plurality of stimulation vectors addressable by a stimulator device, obtaining a set of strength-duration curve data by controlling delivery of electrical stimulation by the stimulator device to determine a threshold pulse amplitude value that evokes a physiological response indicative of target nerve modulation for each one of a plurality of pulse width values, and determining at least one metric from the set of strength-duration curve data. The method further comprises selecting a stimulation vector from the plurality of stimulation vectors for target nerve modulation by the stimulator device based on a comparison between the at least one metric calculated from the set of strength-duration curve data for each stimulation vector of the set of stimulation vectors.

In various examples, a medical device system comprises a stimulator device, and processing circuitry configured to perform any method described herein.

In certain examples, a medical device system comprises a stimulator device coupled to at least one multi-electrode lead and configured to address a plurality of stimulation vectors, wherein at least some of the stimulation vectors include at least one electrode of the at least one multi-electrode lead, and processing circuitry configured to, for each stimulation vector of a plurality of stimulation vectors addressable by a stimulator device, obtain a set of strength-duration curve data by controlling delivery of electrical stimulation by the stimulator device to determine a threshold pulse amplitude value that evokes a physiological response indicative of target nerve modulation for each one of a plurality of pulse width values, and determine at least one metric from the set of strength-duration curve data. The processing circuitry is further configured to select a stimulation vector from the plurality of stimulation vectors for target nerve modulation by the stimulator device based on a comparison between the at least one metric calculated from the set of strength-duration curve data for each stimulation vector of the set of stimulation vectors.

Various examples include at least one of a medical device, system, method and non-transitory computer-readable storage medium comprising executable instructions, for utilizing strength-duration data for electrode targeting and selection as described in the specification and/or shown in any of the drawings.

Some examples include at least one of a medical device, system, method and non-transitory computer-readable storage medium comprising executable instructions, for targeted stimulation or targeted stimulation programming as described in the specification and/or shown in any of the drawings.

In various examples, a medical device or system comprises means for performing any method described herein.

Consistent with certain examples, a non-transitory computer-readable storage medium comprises instructions, that when executed by processing circuitry of a medical device or system, cause the medical device or system to perform any method described herein.

DETAILED DESCRIPTION

Figure 1:
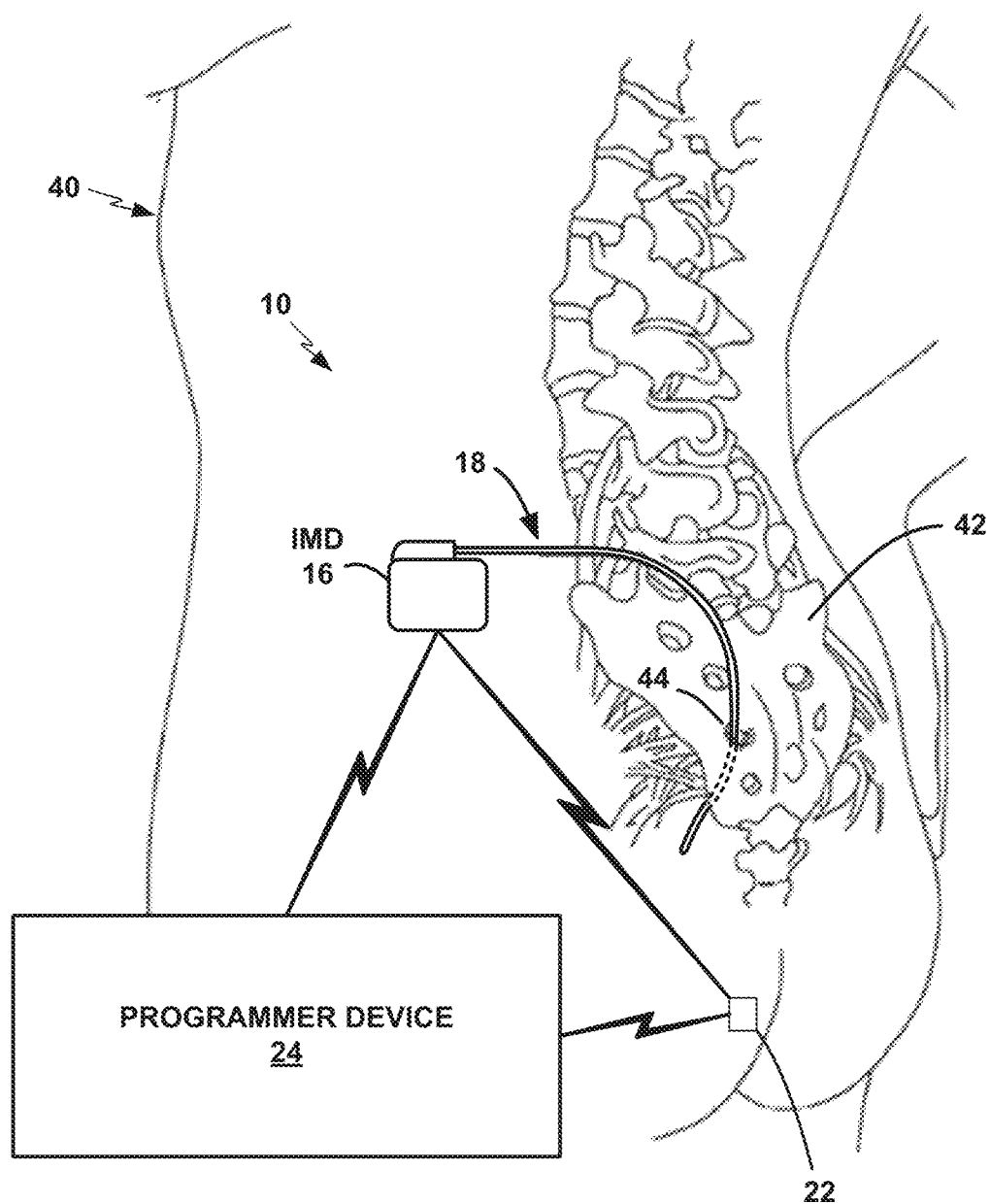
FIG. 1 is a conceptual diagram illustrating an example therapy system that delivers electrical stimulation therapy to a patient, in accordance with certain examples of this disclosure.

As described above, this disclosure describes devices, systems, and techniques for identifying stimulation vectors that are able evoke therapeutic responses in neurons by neurostimulation with efficient pulse widths (pulse durations), which, compared to pulse widths in accordance with the generally recommend values, may be more energy-efficient and/or provide enhanced therapeutic windows in terms of available amplitude range without inducing non-therapeutic side effects. Some examples are directed to certain types of neurostimulation, e.g., sacral neuromodulation (SNM), for managing incontinence (bladder incontinence and/or fecal incontinence) of a patient and/or other patient conditions, such as pelvic or other pain; or spinal cord stimulation (SCS) for managing chronic pain. In some examples, processing circuitry of a medical device system is configured to acquire strength-duration curve data for each of a plurality of stimulation vectors, and select one or more of the stimulation vectors as preferred based on a comparison of vector-specific values for one or more metrics derived from the strength-duration curve data for the vectors. As used herein, a stimulation vector represents a particular configuration for electrodes used to deliver electrical stimulation. For instance, stimulation vectors can be distinguished based upon selection of a different set electrodes on one or more lead and the polarity of the electrical signals relative to the different electrodes. In this manner, different stimulation vectors can be used to deliver the same electrical waveform. As used herein, a strength-duration curve represents a stimulation strength at different pulse durations (also referred to as pulse widths). In particular, the stimulation strength can represent the lowest measured stimulation strength (e.g., current or voltage amplitude) at which a desired physiological response was evoked.

There are a number of different examples, implementations, features, or embodiments discussed herein in various contexts. It is understood that, unless otherwise stated, the different examples, implementations, features, or embodiments can be used in various combinations even where a particular combination has not been expressly recited. As one example, certain aspects of a medical device system described herein relate to stimulation having different pulse durations and to providing different types of therapies. Each possible pulse width or range of pulse durations has not been expressly stated in combination with each type of therapy.

Metrics derived from the strength-duration curve data for a stimulation vector may include area under the curve (AUC) (e.g., expressed as an integral), slope (e.g., expressed as a derivative), or any other metric that characterizes the magnitude, curvature, and/or shape of the strength-duration curve. In general, stimulation vectors better targeted to the neuron target will be flatter, with lower amplitudes necessary for capture, including at shorter pulse-widths. Use of such a stimulation vector to deliver electrical stimulation therapy to a patient may facilitate efficacious stimulation with electrical pulses having more efficient, i.e., shorter pulse widths and/or enhanced therapeutic windows.

For example, a medical device may be configured to deliver electrical stimulation therapy to a patient with electrical pulses having efficient pulse widths and/or enhanced therapeutic windows. For example, a medical device of this disclosure may be configured to deliver electrical stimulation therapy with pulse widths in a range with lower bounds of 20 or 30 microseconds and upper bounds of 60, 180 or 210 microseconds. For instance, a few example ranges include pulse widths of 20 to 210 microseconds, 20 to 180 microseconds, 20 to 60 microseconds, or at another value close to this range, instead of the 210 µs pulse width generally recommended. Stimulation with pulse widths in or proximate to this range may evoke a therapeutic response as is elicited at 210 µs, but using substantially less energy per pulse (e.g., approximately 20% to 90% less energy per pulse), thereby substantially extending (e.g., approximately tripling) the life or the time between recharging of a power source (e.g., a lithium ion battery) for an implanted medical device, and extending the therapeutic range. As used herein, the pulse width represents the time between the rising and falling pulses edges measured at 50% of the pulse amplitude.

Electrical stimulation therapy may include delivery of electrical stimulation of peripheral nerves (e.g., sacral, pudendal, dorsal genital, tibial nerve, and branches of any of the aforementioned nerves) via a medical device. In some examples, the nerve roots of the third sacral foramen (S3) may be targeted in part for neurostimulation. Such electrical stimulation may be used to modify pelvic floor function to treat various patient conditions (e.g., urinary incontinence and fecal incontinence). Although the present disclosure describes application of electrical stimulation using an implantable medical device (IMD), the devices, systems, and techniques of the present disclosure may also be implemented in an external medical device that applies electrical stimulation via implanted or external electrodes.

Additionally, although therapeutic neurostimulation of the sacral nerve for treatment of incontinence is detailed as an illustrative example, the techniques of this disclosure may be applicable to any form of neurostimulation of any neural target. Using neuromodulation, a medical device may deliver electrical stimulation to treat one more undesirable patient conditions associated with muscle contractions, e.g., such as contractions associated with involuntary voiding of the bladder or bowel of a patient. Although some examples of the disclosure are primarily described with regard to managing incontinence, in other examples, the electrical stimulation may be delivered to a patient to decrease the number and/or impact of episodes associated with other patient conditions, such as, e.g., overactive bladder or bowel, irritable bowel, pelvic pain, bowel pain, bladder pain, sacral nerve stimulation (SNS), or spinal cord stimulation (SCS) for other therapeutic purposes such as pain relief in applications other than pelvic pain, and the like.

A medical device may deliver electrical stimulation therapy to a patient according to one or more therapy programs (also referred to herein as a set of electrical stimulation parameter values, e.g., pulse width, amplitude or voltage, frequency). A therapy program may, therefore, be used by a processor to control delivery of electrical stimulation therapy by the medical device (e.g., via one or more electrodes), and may include information identifying which electrodes have been selected for delivery of stimulation according to the therapy program, the polarities of the selected electrodes, e.g., the electrode configuration or stimulation vector for the program, and voltage or current amplitude and frequency of electrical stimulation delivered by the electrodes. In the case of electrical stimulation pulses, the therapy program may specify a pulse rate/frequency and a pulse width/duration. Delivery of electrical stimulation pulses is described below for purposes of illustration.

A configuration setting of the implantable medical device may define the electrical stimulation parameter values that define the electrical stimulation signal. The stimulation parameters can include the signal strength (e.g., a pulse amplitude expressed as a voltage or current), a pulse width (the duration of each pulse), and a pulse rate (e.g., pulses delivered according to a particular frequency), and may also define the duty cycle of electrical stimulation therapy. The duty cycle indicates an "on" time of electrical stimulation therapy (e.g., when electrical stimulation is actively being delivered to the patient) and an "off" time of electrical stimulation therapy (e.g., when no electrical stimulation is actively being delivered by a medical device to the patient). When "on," the system provides stimulation pulses according to the stimulation parameters. When "off," the system stops providing the stimulation pulses. Thus, the duty cycle being referred to is the presence or absence stimulation rather than to the individual pulses and their respective on and off times.

It is has been determined that stimulation using substantially shorter pulse widths than the generally recommended value of 210 μs, e.g., in the range of 30 to 180 μs, may evoke similar therapeutic responses and thus provide similar therapeutic efficacy while using substantially less power and yielding substantially longer life or time between recharging for the power source of an implanted medical device that provides the neurostimulation, as well as increase the amplitude range of a therapeutic window. In particular, it has been determined via in vivo experimental testing with ovine preclinical models that successful therapeutic responses may be evoked in nerve roots at the third sacral foramen (S3) with strength-duration curves characterized by chronaxies of 62 and 74 microseconds in accordance with two different methods of determination, as further described below with reference to FIG. 4. The chronaxies are pulse widths for which the current on a strength-duration curve is twice the rheobase current, where the rheobase is the minimum current to evoke the desired therapeutic response for a very long to indefinitely long pulse width. Therapeutic responses with more power-efficient pulse widths and increased therapeutic windows have also been experimentally observed at pulse widths throughout the range of 30 to 180 μs inclusive, as further described below.

Additionally, given nominal uncertainties in experimental and systematic error ranges, variation in placement of implanted electrodes, anatomical and neurological difference between the animal models and humans, and variation in strength-duration relationships caused by neuropathological disorders in some patients, the experimental findings support an inference that successful therapeutic neurostimulation may be obtained with a pulse width significantly lower than the lowest experimentally validated value of 30 μs, e.g., approximately 5, 10, or 20 μs.

Because delivery of neuromodulation with shorter pulse widths may preserve the power source of a stimulator and increase the therapeutic window, techniques of this disclosure in some examples may involve selecting from among a plurality of therapy vectors based on a comparison of one or more metrics derived from strength-duration curve data for the vectors to enable delivery of neuromodulation with relatively shorter pulse widths via the selected stimulation vector. However, the techniques of this disclosure may include delivering neuromodulation having any values of stimulation parameters, e.g., amplitude, pulse width, and pulse rate, via a stimulation vector selected according to the techniques of this disclosure.

FIG. 1 is a conceptual diagram illustrating an example therapy system 10 that delivers electrical stimulation therapy to a patient 40 alleviate a symptom and/or treat a disorder of patient 40, in accordance with certain examples of this disclosure. Therapy system 10 includes an implantable medical device (IMD) 16, as referred to as a stimulator device, which is coupled to lead 18, sensor device 22, and external programmer 24. Lead 18 is implanted through the third foramen 44 of the patient's sacrum 42 (S3). IMD 16 may have one or more additional leads (not shown in FIG. 1) coupled thereto and implanted through the S3 foramen or at other positions in the body of patient 40. IMD 16 generally operates as a therapy device that delivers electrical stimulation to, for example, a tissue site proximate a pelvic floor nerve, a pelvic floor muscle, the urinary sphincter, or other pelvic floor targets. Pelvic floor nerves include peripheral nerves such as sacral nerves, pudendal nerves and associated branches, and dorsal genital nerves. In some examples, IMD 16 delivers the electrical stimulation therapy to a sacral nerve of patient 40 to inhibit bladder contractions or bowel muscle contractions.

IMD 16 provides electrical stimulation therapy to nerves of patient 40 by generating and delivering electrical stimulation signals to a target therapy site by lead 18 and, more particularly, via electrodes (not shown in FIG. 1) disposed proximate to a distal end of lead 18. (FIG. 1 is not intended to show accurate placement of lead 18 or the electrodes.) For example, IMD 16 may deliver electrical stimulation to nerves of patient 40 to inhibit a bladder contraction or a bowel muscle contraction. In some examples, IMD 16 may delivery the electrical stimulation to patient 40 based on, e.g., sensor data and/or patient input. As certain examples, IMD 16 may detect a bladder contraction based on sensor data and then deliver electrical stimulation based on the detected bladder contraction. According to certain examples, patient 40 may use external programmer device 24 to provide patient input to IMD 16, e.g., indicating an increased probability of unintentional voiding, and IMD 16 may deliver the electrical stimulation to targeted nerves of patient 40 to inhibit bladder contraction based on the patient input.

IMD 16 may be surgically implanted in patient 40 at any suitable location within patient 40, such as near the pelvis. In some examples, the implantation site may be a subcutaneous location in the side of the lower abdomen or the side of the lower back or upper buttocks. IMD 16 has a biocompatible housing, which may be formed from titanium, stainless steel, a liquid crystal polymer, or the like. The proximal end of lead 18 is both electrically and mechanically coupled to IMD 16 either directly or indirectly, e.g., via a respective lead extension. Electrical conductors disposed within the lead bodies of lead 18 electrically connect electrodes to stimulation generation circuitry within IMD 16. In the example of FIG. 1, lead 18 carries electrodes to be positioned through the S3 foramen 44, e.g., proximate a ventral aspect of the S3 foramen, for stimulation of pelvic motor and sensory nerves such as the sacral nerve, or other target therapy sites.

Lead 18 may be surgically or percutaneously tunneled to place one or more electrodes carried by a distal end of lead 18 at a desired pelvic nerve or muscle site, e.g., one of the previously listed target therapy sites such as a sacral nerve or pudendal nerve. In some examples, additional leads (not shown in FIG. 1) may be placed proximate to an exterior surface of the wall of a bladder. Electrodes of lead 18 may deliver stimulation to the same or different nerves. In various examples of therapy system 10, IMD 16 may be coupled to more than one lead that includes electrodes for delivery of electrical stimulation to different stimulation sites within patient 40, e.g., to target different nerves.

The illustrated numbers and configurations of lead 18 and electrodes 29 carried by lead 18 are merely exemplary. Other configurations, i.e., number and position of leads and electrodes, may be used in other examples. For example, IMD 16 may be coupled to additional leads or lead segments having one or more electrodes positioned at different locations in the pelvic region of patient 40. The additional leads may be used for delivering stimulation therapies to respective stimulation sites within patient 40 or for monitoring one or more physiological parameters of patient 40. In an example in which the target therapy sites for the stimulation therapies are different, IMD 16 may be coupled to two or more leads, e.g., for bilateral or multi-lateral stimulation.

System 10 includes an external programmer device 24, as shown in FIG. 1. In some examples, programmer device 24 may be a wearable communication device, handheld computing device, computer workstation, or networked computing device. Programmer device 24 may include a user interface that receives input from a user (e.g., patient 40, a patient caretaker or a clinician). The user interface may include a keypad and a display (e.g., an LCD display). The keypad may take the form of an alphanumeric keypad or a reduced set of keys associated with particular functions of programmer device 24. Programmer device 24 can additionally or alternatively include a peripheral pointing device, such as a mouse, via which a user may interact with the user interface. In some examples, a display of programmer device 24 may include a touch screen display, and a user may interact with programmer device 24 via the touch screen display. It should be noted that the user may also interact with programmer device 24 and/or IMD 16 remotely via a networked computing device.

A user, such as a physician, technician, surgeon, electrophysiologist, or other clinician, may interact with programmer device 24 or another separate programmer (not shown), such as a clinician programmer to communicate with IMD 16. Such a user may interact with a programmer to retrieve physiological or diagnostic information from IMD 16. The user may also interact with a programmer to program IMD 16, e.g., to select values for the stimulation parameter values of the therapy cycle with which IMD 16 generates and delivers electrical stimulation and/or the other operational parameters of IMD 16.

IMD 16 and programmer device 24 may communicate via wireless communication using any of various techniques known in the art. Examples of communication techniques may include, for example, low frequency or radiofrequency (RF) telemetry, but other techniques may also be used. In some examples, programmer device 24 may include a programming head that may be placed proximate to the patient's body near the IMD 16 implant site in order to improve the quality or security of communication between IMD 16 and programmer device 24.

Medical device system 10 is an example of a medical device system configured to implement the techniques described in this disclosure for selecting a stimulation vector based on a comparison of values of a metric determined based on strength-duration curve data obtained for each of the stimulation vectors. Processing circuitry of medical device system 10, such as processing circuitry of IMD 16 or programmer device 24, may control IMD 16 to deliver electrical stimulation via each of a plurality of stimulation vectors to determine strength-duration curve data for each of the stimulation vectors. For each stimulation vector, IMD 16 may deliver stimulation at a plurality of pulse width values, and the processing circuitry may determine the strength-duration curve data by identifying a stimulation strength, e.g., expressed as a threshold pulse amplitude value that evokes a physiological response indicative of target nerve modulation.

In some examples, identifying the threshold amplitude includes detecting activation, e.g., contraction or electrical activity, of a particular muscle evoked in response to stimulation at the threshold. In examples of sacral or other pelvic neuromodulation, activation of the muscles may include activation of pelvic muscles, such as levator ani, anal sphincter, or other muscles associated with anal winking, bellows, perianal, or tail contractions, or muscles associate with plantar flexion of the big toe. The processing circuitry may detect electrical activation of a muscle via one or more electrodes, such as one or more electrodes coupled to IMD 16 via lead 18 or another lead. The processing circuitry may detect contraction of the muscle via one or more sensors, such as accelerometers or strain gauges.

In some examples, the electrodes and/or sensors used to detect activation of a muscle are included as part of sensor device 22. Sensor device 22 may be wirelessly coupled to either or both of IMD 16 and programmer device 24, as illustrated in FIG. 1, or may be coupled to IMD 16 and/or programmer device 24 via a lead or cable. Sensor device 22 may include implanted and/or external electrodes or sensors. In some examples, electrodes and/or sensors used to detect activation of a muscle are included as part of IMD 16 and/or programmer device 24.

Based on the collected strength-duration curve data for each of the stimulation vectors, e.g., a set of threshold amplitude values associated with corresponding pulse width values, the processing circuitry determines a value of one or more metrics. Example metrics include an area under the curve (AUC) (e.g., determined using an integral), or a slope (e.g., determined by taking a derivative at a point on the curve or as a slope between any selected two of the amplitude) values) of the strength-duration curve data. The processing circuitry selects one or more of the stimulation vectors based on a comparison of the metric values, e.g., selects the one or more stimulation vectors having the lowest value(s).

Although illustrated in FIG. 1 as including IMD 16 implanted within patient 40, in other examples a medical device system configured to implement the techniques of this disclosure may additionally or alternatively include an external stimulator device, which may be coupled to implanted or external electrodes, and used to provide therapy on a shorter-term trial, or longer-term, basis.

Figure 2:
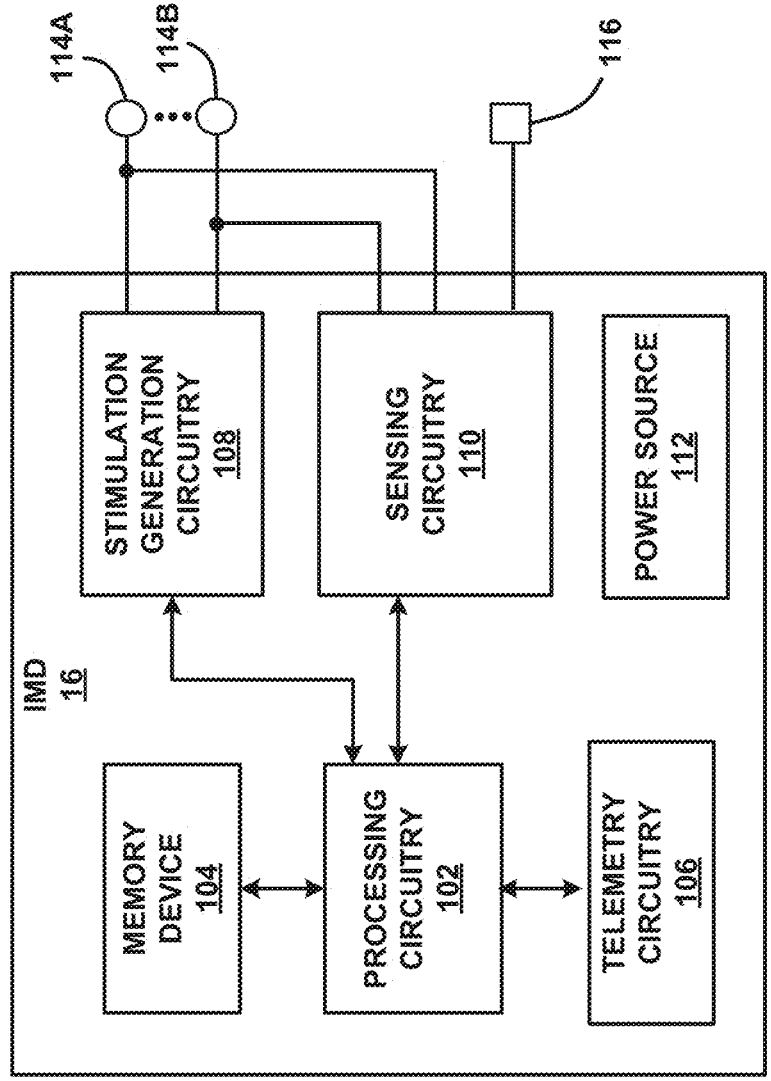
FIG. 2 is a functional block diagram illustrating example components of an implantable medical device (IMD), in accordance with certain examples of this disclosure.

FIG. 2 is a functional block diagram illustrating example components of IMD 16, also referred to as a stimulator device, in accordance with certain examples of this disclosure. In the example of FIG. 2, IMD 16 includes processing circuitry 102, memory device 104, telemetry circuitry 106, stimulation generation circuitry 108, sensing circuitry 110, and power source 112.

Stimulation generation circuitry 108 is configured to generate and deliver electrical stimulation under the control of processing circuitry 102 executing instructions stored on memory device 104. For example, processing circuitry 102 may control stimulation generation circuitry 108 by accessing memory device 104 to selectively access and load therapy programs into stimulation generation circuitry 108. In some examples, stimulation generation circuitry 108 generates therapy in the form of electrical pulses. In other examples, stimulation generation circuitry 108 may generate electrical stimulation in the form of continuous waveforms.

In the example of FIG. 2, stimulation generation circuitry 108 is electrically coupled to electrodes 114A and 114B (collectively, "electrodes 114"). For ease of illustration, two electrodes 114 are depicted in FIG. 2. However, stimulation generation circuitry 108 may be coupled to any number of electrodes 114 provided on one or more leads 18 and/or one or more conductive portions of a housing of IMD 16.

Stimulation generation circuitry 108 is configured to deliver electrical stimulation to a tissue site of patient 40 via different selected combinations of electrodes 114, which may be programmed as anodes or cathodes. A selected combination of electrodes 114 having given polarities may be referred to as a stimulation vector, and stimulation generation circuitry 108 may be configured to deliver stimulation via a plurality of different stimulation vectors. The stimulation generation circuitry 108 may be configured to select or address each of the different stimulation vectors to control the location and polarity of the stimulation relative to the lead 18. As used herein, a stimulation vector is addressable by the stimulation device when the stimulation device is capable of delivering the stimulation using the stimulation vector. A stimulation vector is not addressable when the stimulation device is not capable of delivering the stimulation using the stimulation vector. In some examples, a proximal end of lead 18 extends from the housing of IMD 16 and a distal end of lead 18 (carrying one or more of electrodes 114) extends, such as via the S3 sacral foramen 44, to one or more target therapy sites within the pelvic floor, such as tissue sites proximate to a sacral nerve, a pudendal nerve, a hypogastric nerve, a urinary sphincter, an anal sphincter, or any combination thereof.

Sensing circuitry 110 may be coupled to electrodes 114 and/or sensor(s) 116. Sensing circuitry 110 may include filters and amplifiers, as examples, configured to receive a signal from electrodes 114, e.g., a far-field electromyogram (EGM), and provide an indication to processing circuitry 102 of electrical activation of a muscle of interest based on the signal. In some examples, electrical activation of muscle may be detected as an evoked compound muscle action potential (eCMAP). The eCMAP can be sensed by an electrode or other sensor which is located far from the contracting muscle (i.e., a far-field eCMAP) or which is placed in, or in close proximity to, the activated muscle (i.e., a near-field eCMAP).

In general, evoked compound muscle action potential (eCMAP) is a measure of a muscular response signal generated by the aggregate activity of a group of muscle tissues firing in response to an externally applied electrical stimulation, generally but not limited to electrical stimulation provided to a human patient. In contrast to an eCMAP signal, an eCAP signal is a measure of the aggregate (compound) neural activity of a group of nerves firing in conjunction with each other. An eCAP signal is generally detectable at a time period after application of electrical stimulation that is earlier than the time period when an eCMAP signal generated in response to the same electrical stimulation would be detectable. In addition, the eCMAP signal is a signal that can be sensed within the patient by sensors that are not necessarily located in the same location where the stimulation that caused the eCMAP signal to occur was delivered. The sensors detecting the eCMAP signal also may not be in intimate contact with the muscle tissue or with a location where the electrical stimulation was applied. This ability to sense the eCMAP signal in a location other than were the stimulation was applied is referred to as "far-field" signal detection. An example of far-field detection of an eCMAP signal includes instances where stimulation is applied to the spinal cord (e.g., wherein the electrodes providing the stimulation are located within the epidural fluid of the spinal cord) and the eCMAP signal generated in response to the stimulation applied to the spinal cord is sensed at the para-spinal muscles located outside the bony structure of spinal cord. In some implementations of far-field detection, electrical stimulation is applied using sacral leads implanted in the fatty matter of the sacrum and an eCMAP signal generated by the muscle tissue of the levator ani is detected by sensors located in the pelvic floor of a patient.

Generation of an eCMAP signal by a group of muscle tissue can occur in response to applied stimulation without resulting in an actual contraction of the muscle tissue generating the eCMAP signal. In other words, a patient may not even perceive muscle activity indicated by an eCMAP signal if no muscle contraction occurs. In various examples, detecting an eCMAP signal may thus include detecting an eCMAP signal generated by a group of muscle tissue without having the muscles tissue being stimulated to a level that causes actual muscle contraction of the muscle tissue to occur. The eCMAP signal may thus provide more accurate indications of muscles affected by a delivered stimulation signal. Further, eCMAP signals are detectable when a patient is sedated, wherein other signals such as eCAP or EMG may be less easily detectable in sedated patients.

In some examples, sensing circuitry 110 may detect contraction of the muscle of interest via sensor(s) 116, which may include one or more accelerometers or strain gauges, as examples. Sensor(s) 116 may be included within or on a housing of IMD 16, or connected to IMD 16 via a lead implanted with a distal end proximate to a tissue of interest, e.g., a muscle involved in control of urinary or fecal function. In either case, processing circuitry 108 may detect that a physiological response indicative of target nerve modulation has been evoked based on the signal received by sensing circuitry 110. In some examples, processing circuitry 108 may detect that a physiological response indicative of target nerve modulation has been evoked based on a signal received from sensor device via telemetry circuitry 106.

Telemetry circuitry 106 includes any suitable hardware, firmware, software or any combination thereof for communicating with another device, such as programmer device 24 or sensor device 22 (FIG. 1). Under the control of processing circuitry 102, telemetry circuitry 106 may receive downlink telemetry, e.g., patient input, from and send uplink telemetry to programmer device 24 with the aid of an antenna, which may be internal and/or external. Processing circuitry 102 may provide the data to be uplinked to programmer device 24 and the control signals for the telemetry circuitry 106, and receive data from telemetry circuitry 106.

Processing circuitry 102 may control telemetry circuitry 106 to exchange information with medical device programmer device 24. Processing circuitry 102 may transmit operational information and receive stimulation programs or stimulation parameter adjustments via telemetry circuitry 106. Also, in some examples, IMD 16 may communicate with other implanted devices, such as stimulators, control devices, or sensors, via telemetry circuitry.

The processing circuitry described in this disclosure, such as processing circuitry 102, may be one or more digital signal processors (DSPs), general purpose microprocessors, application specific integrated circuits (ASICs), field programmable logic arrays (FPGAs), or other equivalent integrated or discrete logic circuitry, or combinations thereof. The functions attributed to processing circuitry described herein may be provided by a hardware device and embodied as software, firmware, hardware, or any combination thereof.

Memory device 104 stores instructions for execution by processing circuitry 102. In some examples, memory device 104 may store information regarding patient parameters, e.g., sensed via electrodes 114 and/or sensors 116, collected strength-duration curve data for a plurality of stimulation vectors, and metric values determined from the strength-duration curve data. Memory device 104 may include separate memories for storing instructions, electrical signal information, programs, and other data.

Memory device 104 may include any volatile, non-volatile, magnetic, or electrical media, such as a random access memory (RAM), read-only memory (ROM), non-volatile RAM (NVRAM), electrically-erasable programmable ROM (EEPROM), flash memory, and the like. Memory device 104 may store program instructions that, when executed by processing circuitry 102, cause IMD 16 and processing circuitry 102 to perform the functions ascribed to IMD 16 and processing circuitry 102 herein.

Power source 112 delivers operating power to the components of IMD 16. Power source 112 may include a battery and a power generation circuit to produce the operating power. In some examples, the battery may be rechargeable to allow extended operation. The battery may be a lithium ion or lithium polymer battery, for example. Recharging the battery may be accomplished through proximal inductive interaction between an external charger and an inductive charging coil within IMD 16. In other examples, an external inductive power supply may transcutaneously power IMD 16 whenever stimulation therapy is to occur. As described herein, configuring stimulation generation circuitry 108 to deliver pulses having smaller widths may reduce consumption of the energy stored in power source 112.

IMD 16 and processing circuitry 102 are examples of an IMD or stimulator device and processing circuitry configured to implement the techniques of this disclosure. Processing circuitry 102 of IMD 16 may perform the functions ascribed to processing circuitry herein alone, or in combination with processing circuitry of one or more other devices, such as programmer device 24 or sensor device 22. For example, processing circuitry 102 may control stimulation generation circuitry 108 to deliver electrical stimulation via each of a plurality of stimulation vectors to determine strength-duration curve data for each of the stimulation vectors. For each stimulation vector, processing circuitry 102 may control stimulation generation circuitry 108 to deliver stimulation at a plurality of pulse width values, and the processing circuitry may determine the strength-duration curve data by identifying a threshold amplitude value that evokes a physiological response indicative of target nerve modulation, e.g., as indicated by a signal received by sensing circuitry 110 via electrodes 114 and/or sensor(s) 116. Based on the collected strength-duration curve data for each of the stimulation vectors, e.g., a set of threshold amplitude values associated with corresponding pulse width values, processing circuitry 102 may determine a value of one or more metrics, and select one or more of the stimulation vectors based on a comparison of the metric values.

Figure 3:
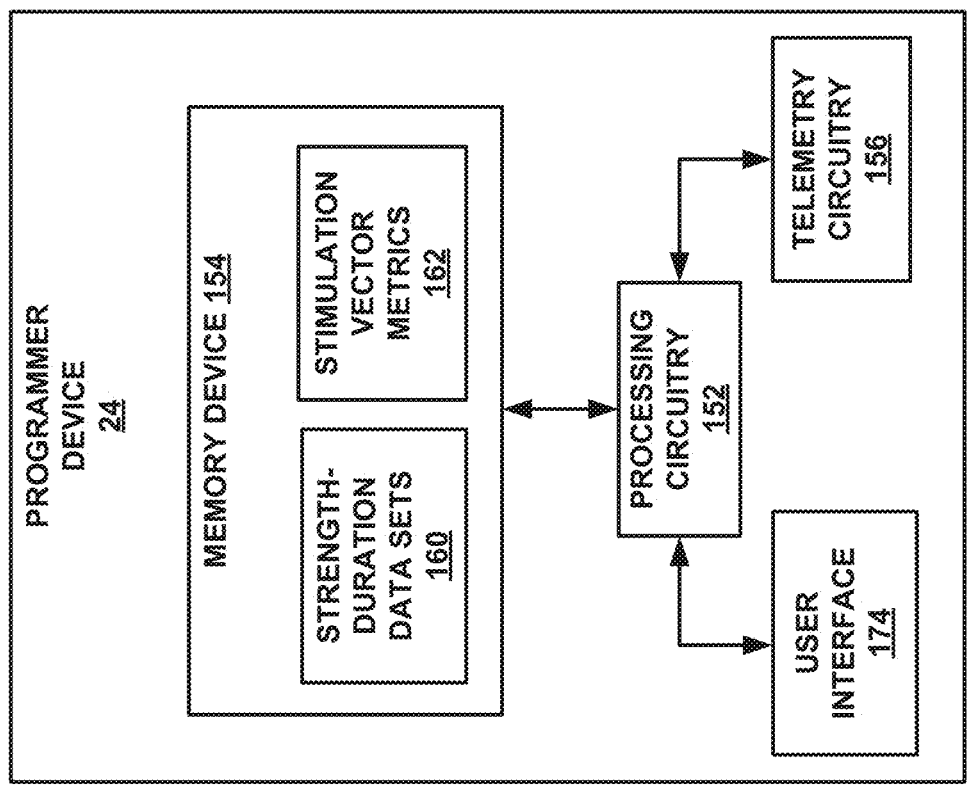
FIG. 3 is a functional block diagram illustrating example components of an external programmer device, in accordance with certain examples of this disclosure.

FIG. 3 is a functional block diagram illustrating example components of external programmer device 24, in accordance with certain examples of this disclosure. While programmer device 24 may generally be described as a handheld computing device, the programmer may be a notebook computer, a mobile computing device such as a mobile phone or tablet computer, a desktop computer, or a workstation, for example. As illustrated in FIG. 3, external programmer device 24 may include a processing circuitry 152, memory device 154, user interface 174, and telemetry circuitry 156. Memory device 154 may store program instructions that, when executed by processing circuitry 152, cause processing circuitry 152 to provide the functionality ascribed to programmer device 24 and processing circuitry 152 throughout this disclosure.

In some examples, memory device 154 may further include therapeutic neurostimulation instructions defining outputs of IMD 16 to implement neurostimulation therapy, similar to those stored in memory device 104 of IMD 16. The therapeutic neurostimulation instructions stored in memory device 154 may be downloaded into memory device 104 of IMD 16. Memory device 154 may include any volatile, non-volatile, fixed, removable, magnetic, optical, or electrical media, such as RAM, ROM, CD-ROM, hard disk, removable magnetic disk, memory cards or sticks, NVRAM, EEPROM, flash memory, and the like. Processing circuitry 152 can take the form one or more microprocessors, DSPs, ASICs, FPGAs, programmable logic circuitry, or the like, and the functions attributed to processing circuitry 152 herein may be embodied as hardware, firmware, software or any combination thereof.

User interface 174 may include a button or keypad, lights, a speaker for voice commands, and a display, such as a liquid crystal (LCD). In some examples the display may be a touch screen. As discussed in this disclosure, processing circuitry 152 may present and receive information relating to stimulation therapy via user interface 174. For example, processing circuitry 152 may receive user input indicating observation of activation, e.g., contraction, of a muscle indicating that a target nerve has been modulated.

Telemetry circuitry 156 supports wireless communication between external programmer device 24 and IMD 16 or sensor device 22 under the control of processing circuitry 152. Telemetry circuitry 156 may also be configured to communicate with sensor device 22 or other devices direct communication through a wired connection. Telemetry circuitry 156 may be substantially similar to telemetry circuitry 106 described above, providing wireless communication via an RF or proximal inductive medium. In some examples, telemetry circuitry 156 may include an antenna, which may take on a variety of forms, such as an internal or external antenna. An external antenna that is coupled to programmer device 24 may correspond to a programming head that may be placed over IMD 16.

Examples of local wireless communication techniques that may be employed to facilitate communication between programmer device 24 and another computing device include RF communication according to IEEE 802.11 or Bluetooth specification sets, infrared communication, e.g., according to an IrDA standard, or other standard or proprietary telemetry protocols. In this manner, other external devices may be capable of communicating with programmer device 24 without needing to establish a secure wireless connection.

Processing circuitry 152 is an example of processing circuitry configured to implement the techniques of this disclosure. Processing circuitry 152 of programmer device 24 may perform the functions ascribed to processing circuitry herein alone, or in combination with processing circuitry of one or more other devices, such as IMD 16 or sensor device 22. For example, processing circuitry 152 may control IMD 16 to deliver electrical stimulation via each of a plurality of stimulation vectors, and determine strength-duration curve data for each of the stimulation vectors. The determined strength-duration curve data sets 160 may be stored in memory device 154. For each stimulation vector, processing circuitry 152 may determine the strength-duration curve data 160 by identifying a threshold amplitude value that evokes a physiological response indicative of target nerve modulation, e.g., as indicated by user input received from user interface 174, or by a signal received from IMD 16 or sensor device 22 via telemetry circuitry 156. Based on the collected strength-duration curve data for each of the stimulation vectors, e.g., a set of threshold amplitude values associated with corresponding pulse width values, processing circuitry 152 may determine a value of one or more metrics 162, and select one or more of the stimulation vectors based on a comparison of the metric values.

Figure 4:
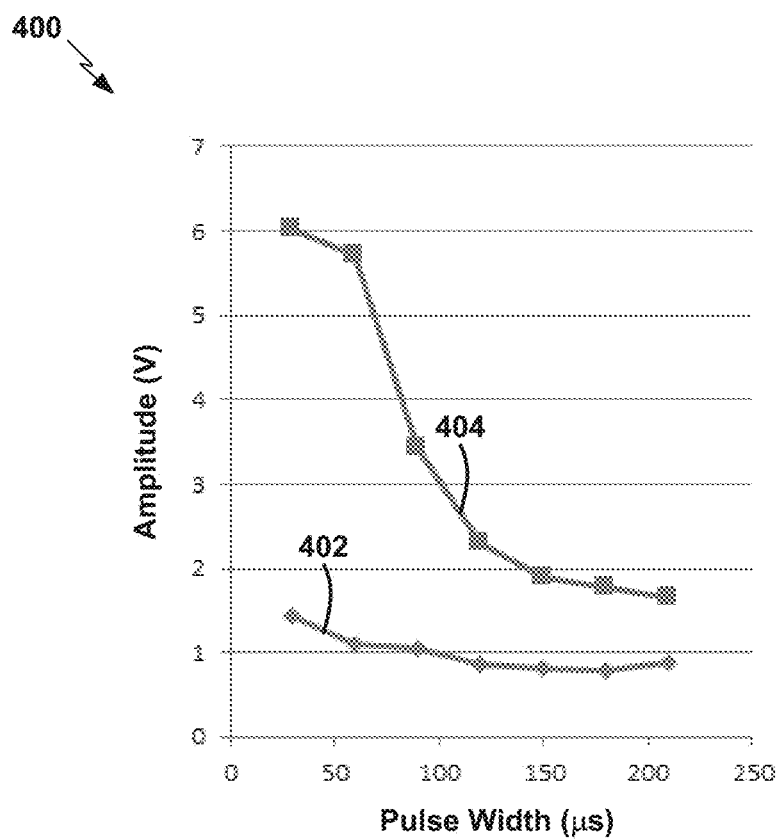
FIG. 4 shows a graph of pulse widths (along the x axis) and amplitudes (along the y axis) of sacral neurostimulation (SNM) that were experimentally determined to evoke therapeutic and non-therapeutic biomarkers, in accordance with certain examples of this disclosure.

FIG. 4 shows a graph 400 of pulse widths (along the x axis) and amplitudes (along the y axis) of sacral neurostimulation (SNM) that were experimentally determined to evoke therapeutic and non-therapeutic biomarkers, in accordance with certain examples of this disclosure. Graph 400 demonstrates successful therapeutic responses at lower pulse widths as well as increased therapeutic windows at lower pulse widths. Graph 400 includes curve 402 drawn between data points for a targeted therapeutic biomarker, and curve 404 drawn between data points for an observed non-therapeutic biomarker. The range of amplitude between the upper curve 404 and the lower curve 402 defines the therapeutic window for each pulse width. The therapeutic biomarker and the non-therapeutic biomarker were tested for and observed at each of various pulse widths, including at 30, 60, 90, 120, 150, 180, and 210 microseconds. That is, for each tested pulse width, the amplitude was increased until the therapeutic biomarker was observed, and then until the non-therapeutic biomarker was also observed.

The therapeutic biomarker is a successful muscle activation, e.g., contraction, that may provide a desired therapeutic effect, such as to inhibit or prevent incontinence, while the non-therapeutic biomarker is a contraction of a proximate muscle that does not provide any therapeutic effect. That is, the non-therapeutic biomarker indicates that the amplitude of stimulation at the selected pulse width is strong enough to evoke contractions in other, nearby muscles that are not targeted for therapeutic stimulation, and thus that that amplitude at that pulse width is undesirably too strong for therapeutic use. The range of amplitude between the successful therapeutic biomarker along curve 402 and the non-therapeutic biomarkers along curve 404 for each pulse width is known as the therapeutic window, because it provides a window or range of options for amplitude that may be used for successful therapy at that pulse width. Different amplitudes may be desired for different applications, and a greater range of available therapeutic amplitudes translates to a greater freedom to apply different amplitudes for different conditions or factors for different therapeutic applications or patients.

One preferred therapeutic biomarker or indicator for successful therapeutic application of neuromodulation to inhibit fecal incontinence, and appropriate sacral neuromodulation (SNM) electrode targeting, is a targeted muscle contraction referred to as an anal wink, which was used as the targeted therapeutic biomarker for curve 402 in graph 400. Occurrence of this targeted muscle contraction may be detected or assessed electrically via electromyography (EMG) or via far-field sensing on a more distal electrode, or it may assessed visually if the stimulation is supra-threshold. Other types of contractions may also serve as preferred indicators for successful therapeutic response to SNM. A positive motor response has been demonstrated to be predictive in achieving a successful treatment. The accuracy of "on-target" response to achieve desired motor response with a lower stimulation intensity may be associated with higher chance of therapeutic success to SNM in clinical practice. Indicators or biomarkers for inappropriate or non-therapeutic targeting include contraction or electrical activation in muscles not innervated via the S3 foramen, such as the semimembranosus or semitendinosus muscle. The indicated points of curve 404 indicate experimentally observed contraction of the semimembranosus muscle.

As graph 400 shows, the therapeutic window is smallest at 210 microseconds, and the lower the pulse width, the larger the larger the therapeutic window. In particular, the lowest two tested pulse widths of 30 and 60 microseconds have a substantially larger therapeutic window than the other values of pulse width higher than 60 microseconds. Additionally, considering only the minimum therapeutic amplitude for each pulse width in itself, some values of pulse width, i.e., 150 and 180 microseconds, have a slightly lower therapeutic amplitude than the generally recommended value of 210 microseconds, which is shown in the data points furthest to the right in graph 400.

Generally, an on-target response threshold in the range of 0.5 to 2.0 volts is preferred in human applications to ensure an adequate space between nerve and the electrode, and to maintain comfort for the patient during stimulation. Thus, in some applications, the upper limit on the therapeutic window can be set at the lower of either the non-therapeutic effect curve 404 or a set maximum amplitude that is selected based upon the preferred target range (e.g., the amplitude value of 2 volts). In this case, the effective therapeutic window may be greatest at about 120 microseconds, with the effective therapeutic window declining in each direction getting further away from 120 microseconds, either lesser or greater than this value. This is relatively independent from the power efficiency of the pulse widths, which is greatest for the lowest viable pulse width (which may potentially be approximately 30 microseconds in this example), and is lower and lower as pulse width gets higher and higher. Some applications may thus optimize both power efficiency and effective therapeutic window given a desired maximum amplitude of 2 volts. As the effective therapeutic window decreases in both directions at 120 microseconds while the power efficiency increases for shorter pulses, the device can be configured to select a value less than 120 microseconds (e.g., anywhere between 30 and 120 microseconds) for the pulse width, depending on the relative importance of each of the two benefits of power efficiency and effective therapeutic window.

Therapeutic efficacy of neurostimulation may also depend on accuracy of placement of electrodes at target locations adjacent to the targeted nerve, and selection of a well-suited stimulation vector across at least two electrodes, as further described below with reference to FIG. 5. The pulse width necessary to evoke a targeted response or biomarker may be achieved at a pulse width much lower than the 210 μs suggested to be used for sacral neuromodulation (SNM) if the electrode is well targeted. Surprisingly, shorter pulse durations have been discovered to provide adequate therapy for SNM. Generating a set of strength-duration curves for different stimulation vectors has been discovered to facilitate selection of stimulation vectors that can be used with shorter pulse durations. This combination has been found to exhibit surprising properties. Short pulse durations at the same pulse rate, have the potential for battery savings in an implanted neurostimulator. In certain instances, it was discovered that the selection of stimulation vectors in connection with short pulse duration can provide benefits that may include, but are not necessarily limited to, an enhanced therapeutic window and a reduction in adverse sensation in the patient receiving SNM.

In experimental testing to determine and characterize SNM strength-duration curves, the SNM stimulation was swept through various pulse widths and various amplitudes at each pulse width, as described above and as shown with the plot points in FIG. 4. One effect observed in sweeping through the pulse widths, as shown in FIG. 4, is the widening therapy window between the targeted therapeutic biomarker (e.g., anal contraction or wink) and the undesirable, non-therapeutic biomarker (e.g., contraction of the semitendinosus muscle) as pulse width gets lower. The therapy window represents the amount that the stimulation amplitude can be increased, relative to the minimum stimulation amplitude for providing the therapeutic response, before introducing one or more undesired effects. In the experimental testing, the undesired effect being measured was the activation of the semitendinosus muscle. A wider therapy window may increase the operating range over which neurostimulation can be delivered to achieve a desired therapeutic response without also causing the undesired effect. This can be particularly useful for reducing the likelihood of the undesired effect occurring during treatment and while also facilitating the setting of the stimulation above the minimum threshold level, thereby reducing the likelihood of not obtaining the desired therapeutic response.

Experimental testing yielded characterizations of the strength-duration curves for various pulse widths for S3 sacral neuromodulation, including characterization of the chronaxie and rheobase of the strength-duration curves. Advantageous values of sacral neuromodulation pulse width were determined based on chronaxies of motor responses to S3 sacral nerve stimulation in experimental sheep models. Electromyography (EMG) responses to SNM with different stimulation pulse widths were examined using voltage amplitudes varying from 0.1 volt (V) to 10 V. The data suggest that a therapeutic motor response may be evoked in the EAS at pulse widths much shorter (e.g., 62 μs to 74 μs) than the 210 μs typically used for SNM. Shorter pulse widths translate directly to increased energy savings in the neurostimulator, among other advantages.

The animal model study involved using implanted medical devices in SNM sheep models to apply neurostimulation to the S3 sacral neuron and to detect, via electromyography (EMG), responsiveness of contraction of the external anal sphincter (EAS) across different pulse widths. Seven trials of six separate S3 nerve roots from four adult, female Polypay sheep were performed. The EMG responses to SNM with different stimulation pulse widths were randomly examined using variable intensities from 0.1 V to 10 V. The strength-duration responses (e.g., as in curve 402 in FIG. 4) as ascertained both from the EAS EMG and via visual detection were fitted with a monoexponential nonlinear regression, which yielded resulting chronaxies of 62.03 μs as detected via EMG and 74.35 μs as detected visually. These data suggest that a similar motor response may be evoked in the EAS at pulse widths much shorter (e.g., in or proximate to a range of 62 μs to 74 μs in some examples) than the 210 μs typically used with SNM. Shorter pulse widths translate directly to increased energy savings in the neurostimulator, among other advantages.

The strength-duration (SD) curve of a nerve, and its key characteristic parameters such as the chronaxie and rheobase, are determined by factors such as the membrane and morphological properties of the excitable tissue, the composition of the nerve fibers, and the distance from the stimulating electrode. The strength-duration curve and its characteristic parameters may also be altered in patients with neuropathological conditions. Thus, in some examples, and particularly considering variation across individual patients, the minimum viable efficacious pulse width in accordance with techniques of this disclosure may be significantly below the lower experimentally determined pulse width value of 30 μs, e.g., 25 or 20 μs.

Figure 5:
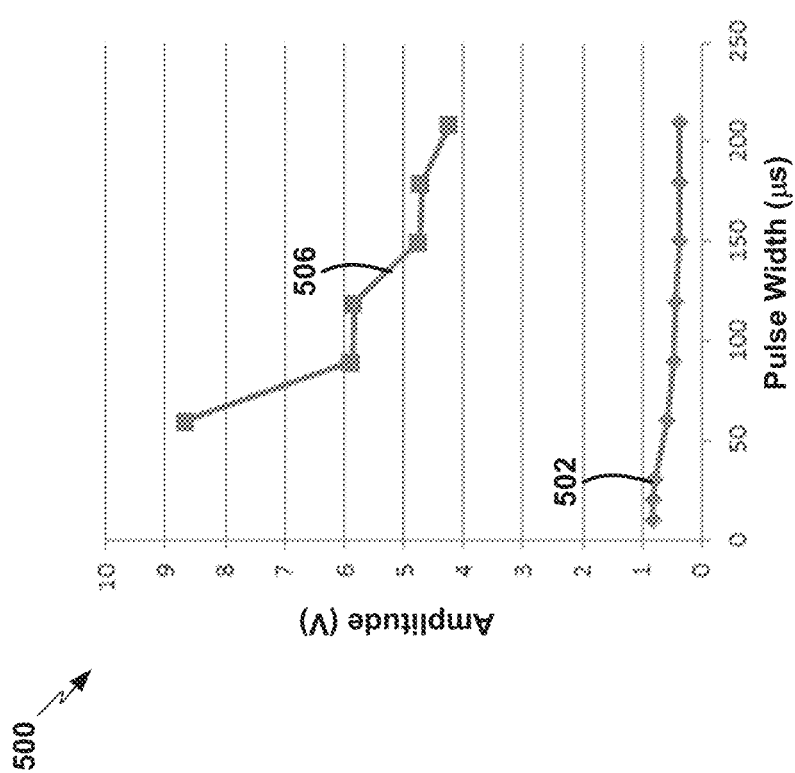
FIG. 5 shows a graph of different strength-duration curve values for evoking a desired therapeutic response with neurostimulation with well-positioned electrodes to provide a well-targeted stimulation vector versus with poorly positioned electrodes providing a sub-optimal stimulation vector, in accordance with certain examples of this disclosure.

FIG. 5 shows a graph 500 of different strength-duration values for evoking a desired therapeutic response with neurostimulation with well-positioned electrodes to provide a well-targeted stimulation vector (curve 502) versus with poorly positioned electrodes providing a sub-optimal stimulation vector (curve 506), in accordance with certain examples of this disclosure. The data shown in FIG. 5 were collected experimentally in a sheep model with a Model 3889 lead manufactured by Medtronic plc, of Dublin, Ireland. inserted through the S3 foramen, and represents the stimulation amplitude and pulse width needed to induce anal contraction, as the targeted therapeutic response in this example. Electrode 3 (the most proximal electrode relative to the stimulator connector) was positioned at the ventral aspect of the S3 foramen, and subsequently closest to the sacral nerve bundle. Electrode 0 was positioned furthest from the S3 sacral nerve bundle. Curve 502 represents results observed for an electrode stimulation vector known as Configuration 2, which is defined as a stimulation vector applied between electrode 3 as the cathode (negative terminal) and electrode 0 as the anode (positive terminal), and is well-targeted with respect to the sacral nerve bundle. Curve 506 represents results observed for an electrode stimulation vector known as configuration C, which is defined as the stimulation vector between electrode 0 as the cathode and electrode 1 as the anode, and which is poorly targeted with respect to the sacral nerve bundle.

As is evident in FIG. 5, the well-targeted stimulation with Configuration 2, as represented by curve 502, results in a relatively flatter (e.g., than curve 506) strength-duration curve with stimulation amplitudes necessary for capture of the therapeutic response all under 1 volt down to 30 μs. Stimulation with Configuration C, as represented by curve 506, does result in capture of the therapeutic response, but only with much higher stimulation amplitudes, sharply so at lower pulse widths (e.g., not until 8.8 volts at 60 μs). Further, for the poorly chosen stimulation vector across the poorly positioned electrodes for the desired therapeutic neurostimulation, all of the amplitude values for minimally evoking the desired response at all the tested pulse widths are above four volts, above the level of two volts which in some examples may be considered a desired ceiling on amplitude to guard against excess patient discomfort. The high values for sufficient neurostimulation in the poor configuration may thus also leave little or no practical therapeutic window, though they may also offer enhanced power efficiency in some examples compared to application of the typical value of 210 μs for pulse width, at least for comparable amplitudes.

The data shown in FIG. 5 thus show the advantage of positioning the electrodes accurately and selecting a superior electrode stimulation vector, that is, which electrodes to use as cathode and anode for the neurostimulation. In some examples, e.g., as part of an initial configuration after IMD 16 has been implanted in a patient, or periodically during use of IMD 16, IMD 16 may also experimentally probe different stimulation vectors, observe responsiveness of the targeted muscle to different electrode stimulation vectors, and select an advantageous stimulation vector for future therapeutic use. For example, IMD 16 may be configured by instructions executed by a processor thereof to run through a program of applying brief test stimulations across different vectors between the different electrodes in their implanted positions. IMD 16 may detect one or more stimulation vectors that yield results similar to curve 506 and one or more stimulation vectors that yield results similar to curve 502. IMD 16 may select a vector that yields results similar to curve 502, or select a vector that evokes efficacious therapeutic responses at low amplitudes, for example.

Figure 6:
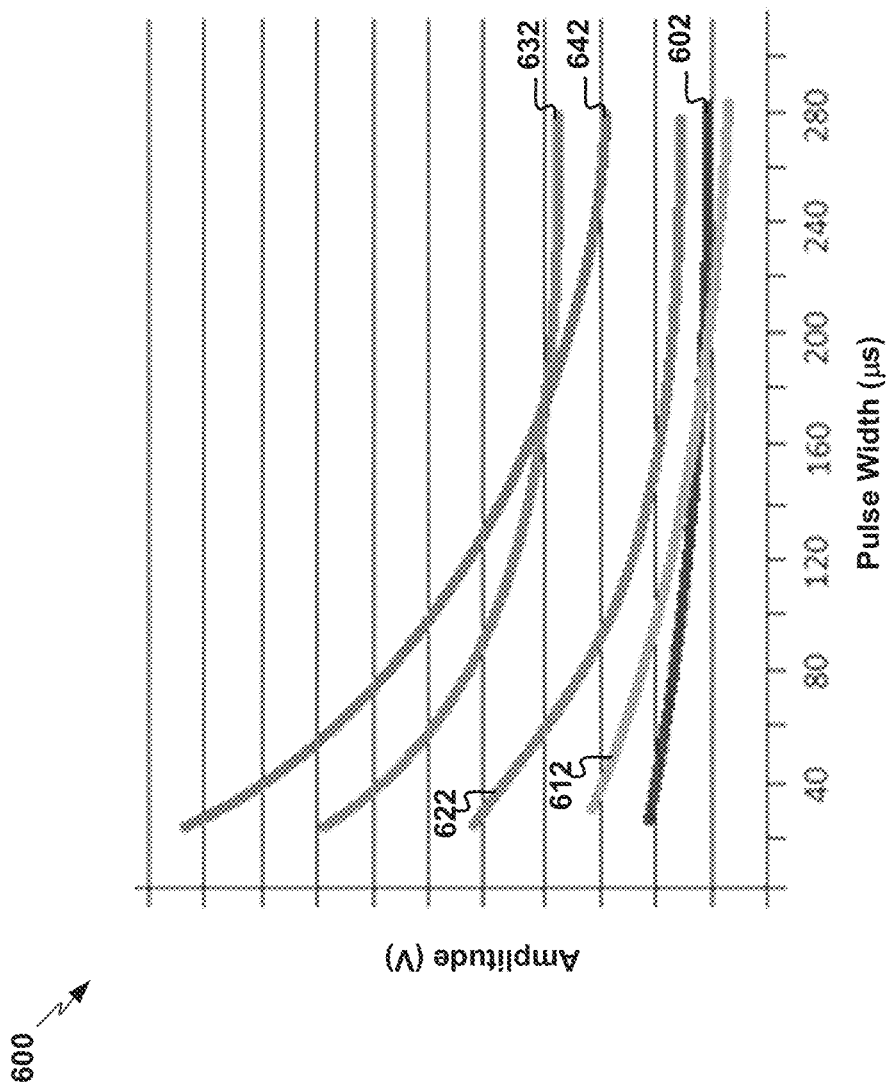
FIG. 6 shows a set of five different strength-duration curves for five different configurations of stimulation vectors that may be detected in response to probing responsiveness to stimulation across five different vectors across four electrodes coupled to an IMD, in accordance with certain examples of this disclosure.

FIG. 6 is a graph 600 illustrating a set of five different strength-duration curves 602, 612, 622, 632, 642 for five different configurations of electrodes, i.e., stimulation vectors, that may be detected in response to probing responsiveness to stimulation across five different vectors across four electrodes coupled to IMD 16, in accordance with certain examples of this disclosure. Processing circuitry of a medical device system including IMD 16 may compare the strength-duration curves (e.g., 602, 612, 622, 632, 642) for any of several or all possible vectors across its attached electrodes, and select an advantageous vector or the most advantageous vector available. The processing circuitry may perform this comparison of vectors and selection of a vector for future normal therapeutic use for a targeted therapy, such as sacral neuromodulation, soon after IMD 16 is implanted in a patient, or at any point thereafter. In some examples, processing circuitry may perform this comparison of vectors using an external stimulator device, such as a trial stimulator coupled to a percutaneous lead prior to implanting IMD 16.

Strength-duration curves 602, 612, 622, 632, 642 characterize five different stimulation vectors known as configurations 2, 4, 7, A and C, respectively on a quadripolar model 3889 lead. The configurations for the respective vectors corresponding to the following configuration of electrical contacts, with 0-3 representing respective contact positioning along the length of the lead: configuration 2: 3−/0+, configuration 4: 2−/0+, configuration 7: 1−/3+, configuration A: 1−/0+, and configuration C: 0−/1+.

The x-axis is the stimulation pulse width, and the y-axis is the amplitude of stimulation needed at a given pulse width to evoke the preferred therapeutic biomarker. The strength-duration curves are representative of strength-duration curve data sets that may be generated automatically (i.e., by running through an algorithm to step through pulse widths and ramp the amplitude up until the evoked potential is detected via EMG or a mechanical force transducer) or manually (by visually observing the presence or absence of an anal contraction). For each strength-duration curve data set, the processing circuitry may determine at least characteristic metric, e.g., the area under the curve (AUC) (e.g., determined by taking the integral of the curve), the curvature, a slope (e.g., determined by taking a derivative at a particular point, or the slope between two or more points of the strength-duration curve data). The particular point used to measure the slope on each curve can be selected using a variety of different techniques. According to certain embodiments, the point on each curve is selected using a consistent approach for each curve so that differences in the determined slopes are indicative of the corresponding differences between the respective curves. For example, using consistent selection of points may allow for the determined slopes to be used as an approximation of the differences in the AUC between the respective curves. In a particular instance, the slope for reach curve can be taken at a particular pulse width. In some instances, the slope for each curve can be taken from the maximum slope within a certain range of pulse widths. Variations from these examples are possible.

In certain embodiments, IMD 16 may select a curve which has the lowest AUC, curvature, blend of curvature/AUC, and/or other characteristic metric or blend of characteristic metrics to enhance or maximize one or more advantageous goals such as increased battery longevity and/or increased therapeutic amplitude window.

According to certain embodiments, a stimulation vector is selected by using the strength-duration curve to identify, for each curve, the combination of stimulation strength (e.g., expressed as a signal amplitude) and pulse width that provide the least power while also meeting a minimum therapeutic window. The curve with the lowest identified power can be selected. Other variations are also possible. For example, the power and therapeutic window for each point on a curve can be used to generate a respective score. The maximum score for each curve can then be compared and used to select the stimulation vector. The scoring can apply different weights to the power and therapeutic window depending on the importance of each factor to the particular therapy. Moreover, the differences in the weightings can vary depending on the particular values. For example, the weight attributable to the size of the therapeutic window can increase, relative to the weighting of the power savings, as the window size decreases (e.g., as the size approaches a minimum threshold value). In other words, differences in the size the therapeutic window become more relevant to the scoring as the size of the window decreases.

Consistent with some embodiments, the therapeutic stimulation levels provided by the IMD are set higher than the minimum strength-duration values determined for the strength-duration curves (e.g., to provide a margin of error relative to the minimum stimulation level). For instance, the stimulation waveform can be set with a higher stimulation amplitude, a longer pulse width, or both. The particular amount of the adjustment could be a fixed amount (e.g., a set amount of voltage), a percentage of the minimum stimulation strength or duration, or set according to a particular formula. In certain embodiments, the system can factor this adjustment into selection of the stimulation vector. For example, the system can determine the amount of power based upon the adjusted (actual) stimulation amplitude as opposed to the power of the strength-duration curve. The determined amount of power can then be used in the selection process.

According to various embodiments, the system is configured to extrapolate the strength-duration curves from a discrete set of measured data points. For example, the system can determine the minimum therapeutic threshold amplitude at particular pulse widths by incrementally increasing (or decreasing) the amplitude at a given set of pulse widths (e.g., every 10 µs). The system can then infer amplitude values for pulse widths between measured values (e.g., using interpolation, polynomial curve fitting, or least squares). The selection process can then use the inferred values on the strength-duration curves when selecting the stimulation vector.

It has been recognized that the AUC can be correlated to the amount of power consumed by the stimulation and to the size of the therapeutic window. According to particular embodiments, the correlation allows for the use of the AUC in select the stimulation vector, e.g., by selecting the stimulation vector with the lowest value for an AUC. In some embodiments, the AUC can be calculated by taking an integral of the strength-duration curve. For example, the AUC could be calculated by taking the continuous interval of a polynomial function that is fit to the measured values. The AUC (or an approximation thereof) can also be calculated using other methods, such as treating the measured values as discrete values and summing the values. The ability to use the AUC in the selection process can be particularly useful for reducing the complexity of the selection process, which can be advantageous for reducing processing power and time used to select the stimulation vector.

Figure 7:
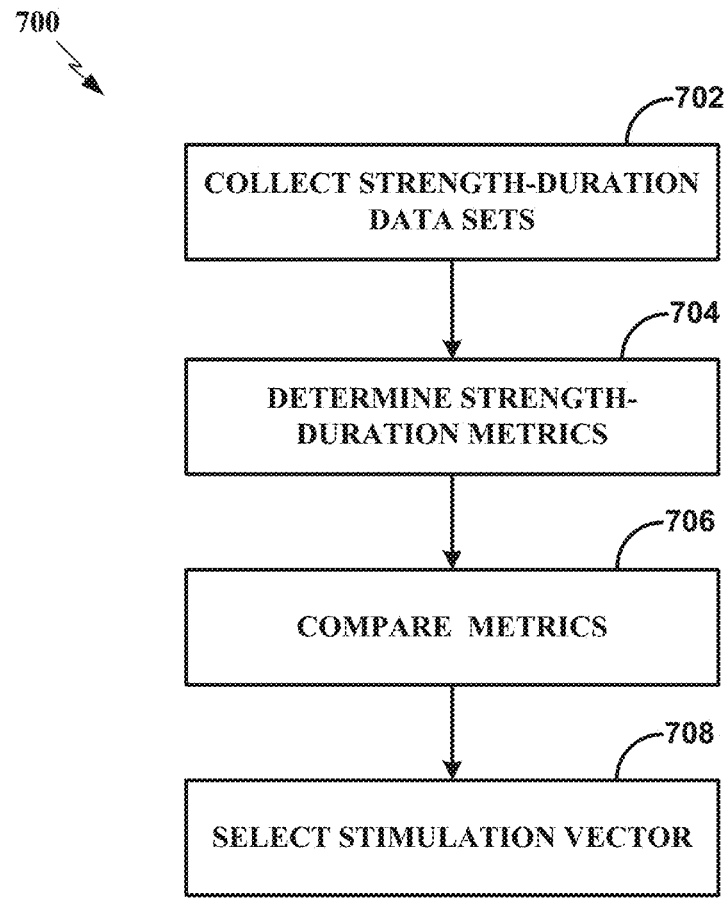
FIG. 7 is a flow diagram of an example technique for selecting a stimulation vector from a plurality of stimulation vectors based on a comparison of strength-duration curve metrics for the stimulation vectors, in accordance with certain examples of this disclosure.

FIG. 7 is a flow diagram of an example technique 700 for selecting a stimulation vector from a plurality of stimulation vectors based on a comparison of strength-duration curve metrics for the stimulation vectors, in accordance with certain examples of this disclosure. The example technique of FIG. 7 may be performed by processing circuitry of a medical device system 10, such a processing circuitry 102 of IMD 16 and/or processing circuitry 152 of programmer device 24.

According to the example of FIG. 7, the processing circuitry collects strength-duration data sets 160 for a plurality stimulation vectors that are addressable by a stimulator device, such as IMD 16 (702). For the collection purposes, the processing circuitry may be configured to use all addressable stimulation vectors or to use a particular subset thereof. The processing circuitry determines, for each of the stimulation vectors, respective values for one or more metrics based the strength-duration curve data for the metric (704). Example metrics include an AUC (e.g., measured as an integral), a curvature metric, a derivative at a particular point on the curve, or a slope between two points on the curve, e.g., between the threshold amplitude values at two pulse widths, such as between two pulse widths below 150 µs, or two pulse widths below 100 µs. The processing circuitry compares the values of the one or more metrics for the different stimulation vectors to each other (706). The processing circuitry selects one or more stimulation vectors based on the comparison, e.g., selects a stimulation vector having a desirable (lowest or highest) value of a metric, such as AUC or slope (708), or score derived from multiple of metrics, such as a combination of power efficiency (pulse duration) and AUC or slope. The stimulator device is then programmed to use a selected stimulation vector, a selected pulse duration, or both the selected stimulation vector the selected pulse duration.

Figure 8:
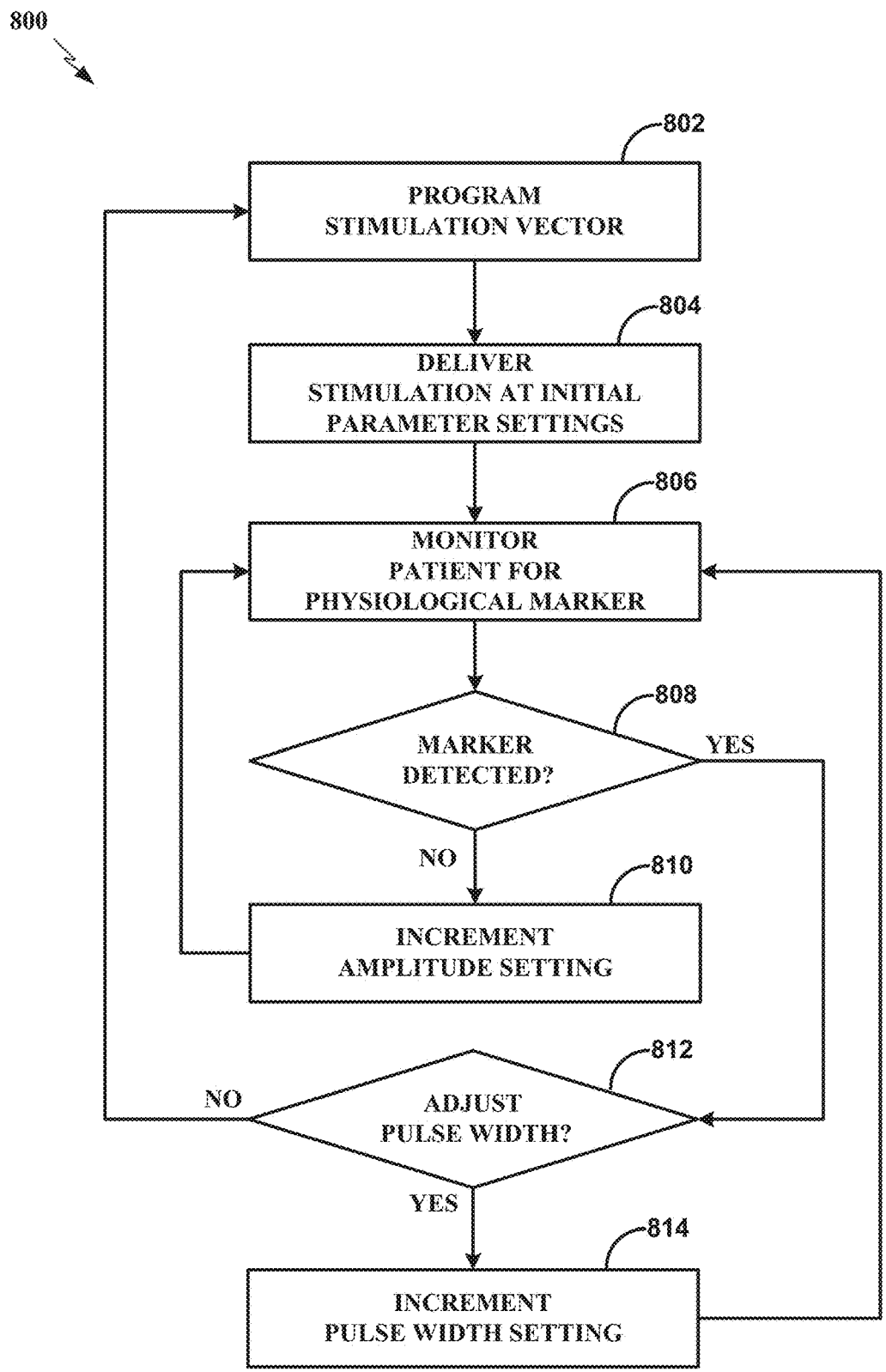
FIG. 8 is a flow diagram illustrating an example technique for collecting strength-duration curve data for a plurality of stimulation vectors, in accordance with one example of this disclosure.

FIG. 8 is a flow diagram illustrating an example technique 800 for collecting strength-duration curve data for a plurality of stimulation vectors, in accordance with certain examples of this disclosure. The example technique of FIG. 7 may be performed by processing circuitry of a medical device system 10, such a processing circuitry 102 of IMD 16 and/or processing circuitry 152 of programmer device 24, and a stimulator device, such as IMD 16.

According to the example technique of FIG. 8, the processing circuitry programs one of the plurality of stimulation vectors (802), and controls IMD 16 to deliver electrical stimulation at initial settings for pulse amplitude and width via the programmed stimulation vector (804). The processing circuitry then monitors the patient for a physiological marker, e.g., activation of a muscle, indicative of effective stimulation of the neural target, e.g., the sacral nerve proximate the S3 foramen (806).

If the physiological marker is not detected (NO of 808), the processing circuitry controls IMD 16 to increment pulse amplitude (810) while holding pulse width at the current setting, and again monitors for the physiological marker (806). The amplitude at which the physiological maker (806) is detected can then be stored for use in generating the strength-duration curve for the current stimulation vector. The particular physiological marker being monitored can be selected based upon various factors, including the therapy being provided. For example, SCS therapy might result in the selection of a physiological marker associated with the relief of pain.

If the physiological marker is detected (YES of 808), the processing circuitry determines whether additional pulse widths to test for the current stimulation vector (812). For example, the processing circuitry can perform a sweep of a set number of different pulse widths for each stimulation vector. In such examples, the determination can be based upon whether each of the pulse widths in the set has been tested using the current stimulation vector.

If there are additional pulse widths to test for the current stimulation vector (YES of 812), the processing circuitry adjusts pulse width to one of the remaining values to test (814) and, in some instances, decrements pulse amplitude, e.g., to the initial setting. If a threshold amplitude value has been determined for all pulse width values desired to complete the strength-duration curve data for the current stimulation vector (NO of 812), the processing circuitry may program IMD 16 to deliver electrical stimulation via another of the plurality of electrode vectors (802).

In some embodiments, the processing circuitry be configured to set an upper limit for the stimulation amplitude (e.g., 2.0 volts). If the upper limit is reached and no physiological marker is detected (equivalent to YES of 808) the processing circuitry stops testing at the current pulse width and determines whether there are additional pulse widths to test (812). In some implementations, the processing circuitry may be configured to determine that additional pulse widths need not be tested for that vector. For instance, the processing circuitry is configured to incrementally reduce the pulse widths. Once the upper limit is reached, the processing circuitry may stop reducing pulse widths under the assumption that reducing the pulse width with result in increased amplitude for the response threshold (e.g., as consistent with the strength-duration curves shown in FIG. 6).

According to some embodiments, the collection of strength-duration curve data can occur during an initiation phase that occurs after implantation of the corresponding lead. The system can then use this information to select the appropriate stimulation vector as well as selecting the desired pulse width and signal amplitude. Various embodiments are also directed toward a system that is configured to allow for subsequent collection of strength-duration curve data. For example, the system can be configured to collect strength-duration curve data in response to a command from a programmer, or periodically (e.g., once a month).

Various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, electrical stimulators, or other devices. The term "processor" or "processing circuitry" may generally refer to any of the foregoing logic circuitry, alone or in combination with other logic circuitry, or any other equivalent circuitry.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. Computer-readable media may include computer-readable storage media forming a tangible, non-transitory medium. Instructions may be executed by one or more processors, such as one or more DSPs, ASICs, FPGAs, general purpose microprocessors, or other equivalent integrated or discrete logic circuitry. Accordingly, the term "processor," as used herein may refer to one or more of any of the foregoing structure or any other structure suitable for implementation of the techniques described herein. The parameters associated with factors such as the pulse widths, amplitude or voltage, frequency, electrode placement, stimulation vectors, or other parameters or factors as described above may be stored in memory of the IMD or in memory of another device, and used by processing circuitry 102 to control delivery of the electrical stimulation therapy.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

Various aspects of the disclosure have been described. These and other aspects are within the scope of the following claims.

What is claimed is:

1. A method of programming an implantable medical device (IMD) of a medical device system, the IMD configured to provide electrical stimulation using a plurality of stimulation vectors and a plurality of pulse widths to a neural target, the method comprising:
    comparing, by the medical device system, strength-duration curve data for the plurality of stimulation vectors to one another, the strength-duration curve data representing, for respective pulse widths and stimulation vectors, a corresponding stimulation strength that evokes a physiological response associated with the neural target;
    determining, by the medical device system, for each of the strength-duration curves, respective values for at least one metric, wherein the metric is selected from the group consisting of: area under the curve, curvature, or slope;
    selecting at least one stimulation vector of the plurality of stimulation vectors based on the comparison of the strength-duration curve data for the plurality of stimulation vectors; and
    programming, by the medical device system and in response to the selection, the IMD to deliver the electrical stimulation to the neural target via the selected at least one stimulation vector,
    wherein, the selection of the at least one stimulation vector is based on a comparison between the values of the at least one metric.

2. The method of claim 1, further comprising:
    creating a strength-duration curve for each of the plurality of stimulation vectors by:
        delivering, by the IMD, electrical stimulation at different threshold pulse amplitudes; and
        determining, by the medical device system, a threshold pulse amplitude value that evokes the physiological response for each one of the plurality of pulse width values.

3. The method of claim 2, further comprising:
    selecting, based upon the comparison, a pulse width between 30 microseconds and 210 microseconds, and programming the IMD to deliver electrical stimulation to the neural target at the selected pulse width.

4. The method of claim 3, wherein the selected pulse width is within a range from 30 microseconds to 120 microseconds and the neural target includes sacral nerves.

5. The method of claim 3, wherein the pulse width is within a range from 60 microseconds to 80 microseconds.

6. The method of claim 2, wherein determining the strength-duration curve for each of the plurality of stimulation vectors comprises detecting the physiological response by monitoring for activation of a particular muscle evoked in response to the electrical stimulation at the threshold pulse amplitude value.

7. The method of claim 6, wherein monitoring for the activation of the particular muscle comprises detecting activation of one or more muscles that cause at least one of: an anal wink, bellows response, or plantar flexion of the big toe.

8. The method of claim 1, wherein the neural target is selected from the group consisting of a sacral nerve and a spinal cord.

9. The method of claim 1, wherein the neural target is a sacral nerve proximate to an S3 foramen.

10. The method of claim 1, wherein the physiological response is associated with alleviating at least one patient condition selected from the group consisting of: urinary incontinence, fecal incontinence, and pain.

11. A method of programming an implantable medical device (IMD), the IMD configured to provide electrical stimulation using a plurality of stimulation vectors and a plurality of pulse widths to a neural target, the method comprising:
    comparing, by the IMD, strength-duration curve data for the plurality of stimulation vectors to one another, the strength-duration curve data representing, for respective pulse widths and stimulation vectors, a corresponding stimulation strength that evokes a physiological response associated with the neural target;
    determining, by the medical device system, for each of the strength-duration curves, respective values for at least one metric, wherein the metric is selected from the group consisting of: area under the curve, curvature, or slope;
    selecting, by the IMD, at least one stimulation vector of the plurality of stimulation vectors based on the comparison of the strength-duration curve data for the plurality of stimulation vectors, wherein the selection of the at least one stimulation vector is based on a comparison between the values of the at least one metric; and
    causing the IMD to deliver the electrical stimulation to the neural target using the selected at least one stimulation vector.

* * * * *